(12) United States Patent
Cochran et al.

(10) Patent No.: US 6,870,060 B1
(45) Date of Patent: Mar. 22, 2005

(54) PRODUCT RECOVERY FROM SUPERCRITICAL MIXTURES

(75) Inventors: Robert N. Cochran, West Chester, PA (US); Jay F. Miller, Chester Springs, PA (US)

(73) Assignee: Arco Chemical Technology, L.P., Greenville, DE (US)

( * ) Notice: Subject to any disclaimer, the term of this patent is extended or adjusted under 35 U.S.C. 154(b) by 0 days.

(21) Appl. No.: 10/691,142

(22) Filed: Oct. 22, 2003

(51) Int. Cl.$^7$ ............................................. C07D 301/02
(52) U.S. Cl. ...................... 549/541; 568/959; 549/542
(58) Field of Search ................................ 549/542, 541; 568/959

(56) References Cited

U.S. PATENT DOCUMENTS 6,710,192 B2 * 3/2004 Hancu et al. ............... 549/512
2003/0161780 A1 8/2003 Howard et al.

OTHER PUBLICATIONS

Allan F.M. Barton, Ph.D. "CRC Handbook of Solubility Parameters and Other Cohesion Parameters" pp. 119–138 1991 CRC Press.

* cited by examiner

Primary Examiner—Amelia A. Owens
(74) Attorney, Agent, or Firm—William C. Long

(57) ABSTRACT

Oxidation products are recovered from a mixture of the products in a dense phase or supercritical solvent by a liquid—liquid extraction at dense phase conditions.

8 Claims, 1 Drawing Sheet

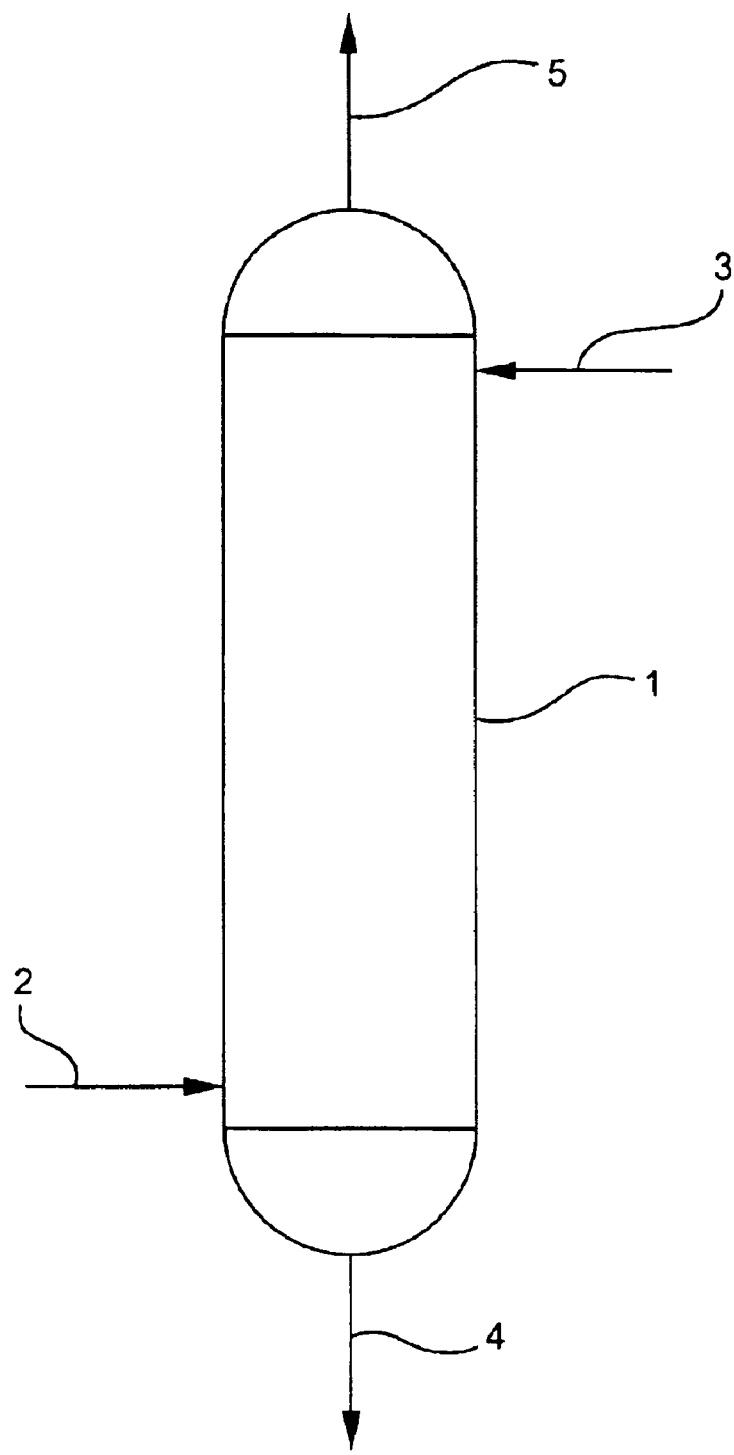

PRODUCT RECOVERY FROM SUPERCRITICAL MIXTURES

FIELD OF THE INVENTION

The present invention relates to the recovery of products such as propylene oxide from reaction product mixtures comprised of a supercritical solvent such as supercritical carbon dioxide propane or propylene without the need for substantial decompression of the supercritical solvent, the recovery being accomplished by a solvent extraction process.

BACKGROUND OF THE INVENTION

Processes have been developed for the production of important chemicals such as propylene oxide which involve the use of dense phase or supercritical solvents such as supercritical $CO_2$ or supercritical propane or propylene. In this regard reference is made to co-pending U.S. application Ser. No. 09/981,198 filed Oct. 16, 2001, the disclosure of which is incorporated herein in its entirety.

In such processes, the desired product can readily be recovered from the reaction mixture by decompression and vaporization of the solvent. However, for economic reasons it is necessary that the solvent be recovered and reused. Where the solvent has been vaporized in the separation, it is necessary that costly recompression and/or refrigeration procedures be used for recovery and reuse of the solvent.

The present invention provides an improved procedure whereby decompression of the reaction mixture and recompression of the solvent can be substantially avoided.

SUMMARY OF THE INVENTION

In accordance with the present invention, a reaction mixture at supercritical or dense phase conditions is contacted with a relatively non-compressible extraction liquid such as water which is substantially immiscible with the supercritical solvent and in which the reaction products are selectively soluble. The supercritical solvent can be separated for reuse, and the extracted reaction products can be recovered by distillation.

BRIEF DESCRIPTION OF THE DRAWING

The attached drawing illustrates a practice of the invention.

DETAILED DESCRIPTION

The present invention can be illustrated by reference to the production of propylene oxide as described in application Ser. No. 09/981,198 filed Oct. 16, 2001. Referring to the drawing, column 1 is a conventional liquid—liquid extraction column which provides for intimate contact and mixing of counterflowing immiscible liquid streams. A reaction mixture comprised of product propylene oxide in carbon dioxide solvent at dense phase or supercritical conditions is introduced to column 1 via line 2 and an aqueous extractant stream is introduced into column 1 via line 3. In column 1, the heavier aqueous stream passes downwardly whereas the lighter carbon dioxide stream passes upwardly through the column. In column 1, intimate contact of the streams is achieved by conventional techniques and as a result of this contact product propylene oxide and other water soluble materials are extracted into the aqueous extractant from the carbon dioxide stream. The extract stream containing the extracted products is removed from column 1 via line 4 while the supercritical carbon dioxide stream depleted in propylene oxide is removed from column 1 via line 5.

An outstanding advantage of practice of the invention is that the carbon dioxide stream removed via line 5 is at essentially the supercritical reaction pressure employed in the production of propylene oxide and thus this stream can effectively be recycled to the epoxidation reactor with only a minimum of treatment.

The extract stream removed via line 4 is readily treated as by distillation for the separation of the various components and recovery of propylene oxide. The aqueous extractant after removal of propylene oxide and other materials can be recycled.

In carrying out the invention, selection of an appropriate extraction solvent is a critical consideration. Generally speaking, suitable solvents for use in the invention are those having the total solubility parameter as defined by Hoy in "Handbook of Solubility Parameters and Other Cohesion Parameters," Barton, portion of the solubility parameter greater than 15 $MPa^{0.5}$. See Table 18 at pages 123–138 of the above publication. For reasons of cost, availability and effectiveness, water and acetonitrile, especially water, are preferred solvents. Mixtures of various solvents can be used.

As above indicated, preferred reaction mixtures which are treated according to the invention are those containing propylene oxide resulting from the reaction of propylene, oxygen and hydrogen using a noble metal on titanium silicalite catalyst in carbon dioxide. Such reaction mixtures generally comprise between 50 and 99 wt. percent solvent, and preferably between 65 and 95 wt. percent solvent. Small amounts of oxygenated by-products can be contained in the reaction mixtures as well as unreacted propylene. Generally the reaction mixtures are at temperatures of 20 to 100° C. and pressures of 65 to 300 atm.

The solvent extraction is carried out at the dense phase or supercritical conditions whereby the advantageous product separation is achieved without the necessity for substantial recompression of the solvent.

The following example illustrates practice of the invention.

Referring to the attached drawing, a reaction mixture containing propylene oxide from the supercritical reaction of propylene, oxygen and hydrogen in carbon dioxide solvent as described in SN 09/981,198 is introduced into extraction column 1 via line 2. The reaction mixture is at 60° C. and 135 atm and comprises by weight 10% propylene oxide, 70% carbon dioxide, 10% propylene and 10% other components.

Water is introduced via line 3 into column 1 at the rate by weight of about 50% of the feed rate. Conditions maintained in column 1 are 60° C. and 135 atm, and the feed materials are intimately admixed therein in accordance with conventional procedures.

An extract stream is removed from column 1 via line 4. This stream comprises by weight 14% propylene oxide and 80% water together with 6% other components and passes to a conventional distillation separation procedure (not shown) for recovery of the product propylene oxide. After this separation, the water extractant is conveniently recycled to the extraction.

A dense phase carbon dioxide stream is removed from column 1 via line 5; this stream comprises by weight 85% carbon dioxide, 12% propylene and 3% others and is conveniently recycled to the epoxidation reaction.

Through practice of this process, more than 95% of the produced propylene oxide recovered in the aqueous extraction stream.

We claim:

1. The process for the separation of oxidation products from a reaction mixture comprised of said products in a solvent at dense phase conditions wherein the reaction mixture is contacted with an extraction solvent which is substantially immiscible with the dense phase solvent and separating a liquid phase containing the oxidation products from a dense phase solvent stream.

2. The process of claim 1 wherein the extraction solvent has a total solubility parameter greater than 24 $MPa^{0.5}$ with the hydrogen bonding portion of the solubility parameter greater than 15 $MPa^{0.5}$.

3. The process of claim 1 wherein the dense phase solvent is carbon dioxide.

4. The process of claim 1 wherein the dense phase solvent is propane.

5. The process of claim 1 wherein the dense phase solvent is propylene.

6. The process of claim 1 wherein the oxidation products comprise propylene oxide.

7. The process of claim 1 wherein the immiscible solvent is an aqueous solvent.

8. The process of claim 1 wherein the immiscible solvent is acetonitrile.

* * * * *